(12) United States Patent
Perret, Jr.

(10) Patent No.: US 6,994,548 B2
(45) Date of Patent: Feb. 7, 2006

(54) GINGIVAL TISSUE RETRACTOR

(76) Inventor: Gerard A. Perret, Jr., 16014 Penwood Dr., Tampa, FL (US) 33647

( * ) Notice: Subject to any disclaimer, the term of this patent is extended or adjusted under 35 U.S.C. 154(b) by 36 days.

(21) Appl. No.: 10/358,725

(22) Filed: Feb. 5, 2003

(65) Prior Publication Data

US 2004/0152043 A1  Aug. 5, 2004

(51) Int. Cl.
*A61C 3/00* (2006.01)
(52) U.S. Cl. ...................................... 433/141
(58) Field of Classification Search ................ 433/141, 433/142, 143; 600/214, 210, 217, 235, 237, 600/242
See application file for complete search history.

(56) References Cited

U.S. PATENT DOCUMENTS

| | | | | |
|---|---|---|---|---|
| 881,722 A | * | 3/1908 | Sausser | 433/144 |
| 1,109,924 A | * | 9/1914 | Hoffman et al. | 433/144 |
| 1,497,749 A | * | 6/1924 | Diack | 433/144 |
| 1,691,786 A | * | 11/1928 | Roth | 433/143 |
| 4,004,345 A | | 1/1977 | Ely | 32/36 |
| 4,747,777 A | * | 5/1988 | Ward | 433/141 |
| 4,854,867 A | * | 8/1989 | Meinershagen | 433/40 |
| 6,045,360 A | * | 4/2000 | Simoes | 433/141 |
| 6,482,152 B2 | * | 11/2002 | Kim | 600/210 |
| 6,575,749 B1 | * | 6/2003 | Greenwald | 433/141 |
| 6,705,865 B1 | * | 3/2004 | Szymaitis | 433/141 |

* cited by examiner

*Primary Examiner*—Todd E. Manahan
(74) *Attorney, Agent, or Firm*—Pendorf & Cutliff

(57) ABSTRACT

A dental tool for retracting gingival tissue is provided that includes a shaft and a working end member, the working end member having an operative end including a first portion sufficiently narrow to retract tissue from a groove of a tooth and a second portion, adjacent the first portion, and being sufficiently wide to retract tissue from an area of the tooth adjacent the groove. A method for retracting gingival tissue is also disclosed.

20 Claims, 2 Drawing Sheets

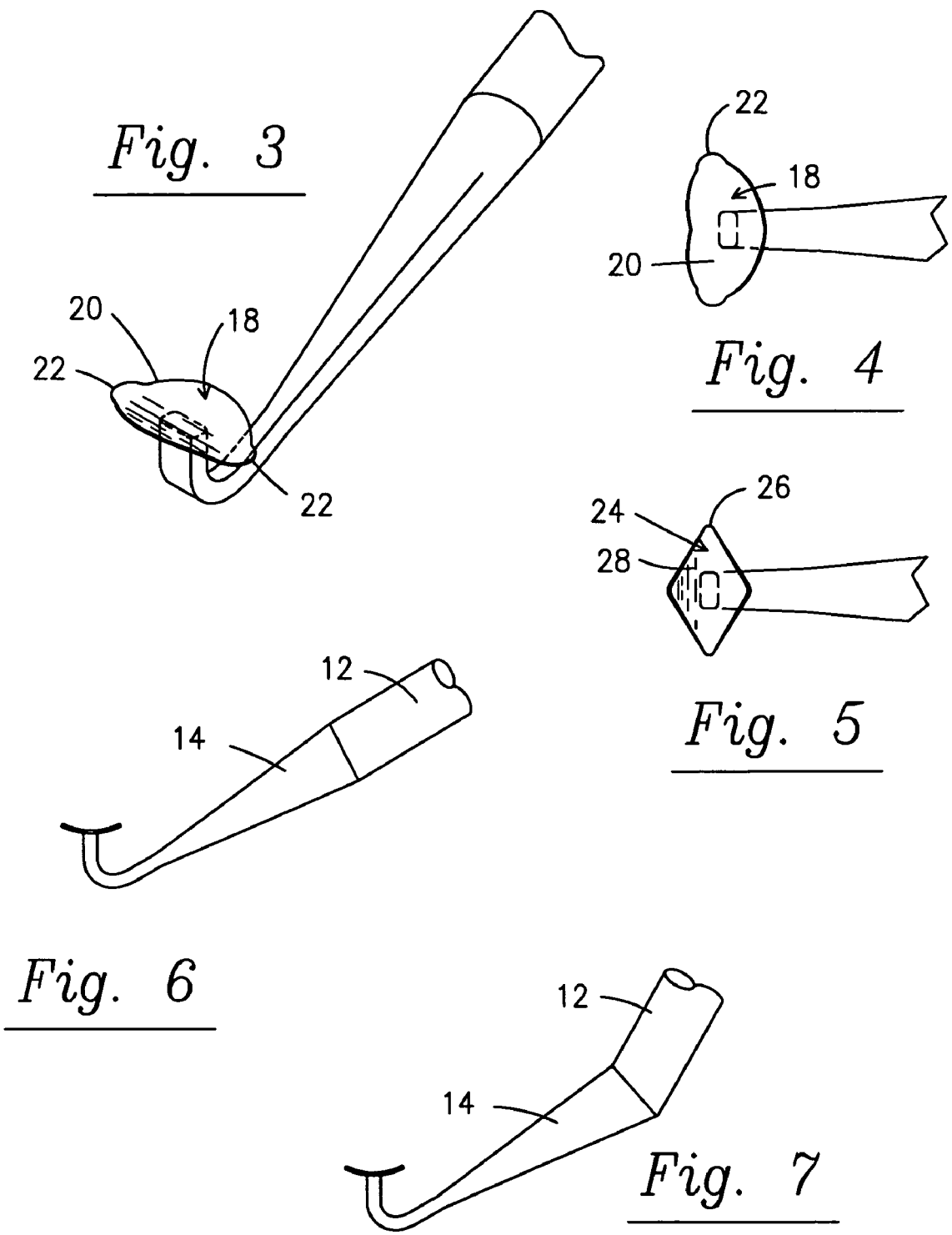

GINGIVAL TISSUE RETRACTOR

FIELD OF THE INVENTION

The present invention concerns a tissue retractor and, in particular, a gingival tissue retractor and, more specifically, a gingival tissue retractor which is particularly suited for retracting gingival tissue as an aid in fitting orthodontic appliances, and a method for retracting such tissues.

BACKGROUND OF THE INVENTION

During the course of orthodontic treatment, small appliances and attachments, commonly known as "braces", are affixed to the teeth of the patient. While there are various types of such appliances and attachments available for use in orthodontic treatment, for the purposes of the current invention and its application, our discussion is limited to an attachment method or "brace" known in the trade as a band. A band is a one-piece ring, made of a thin metal alloy, to which various orthodontic attachments can be welded or soldered. An orthodontic band is designed to fit around the circumference of a tooth in much the same manner as a ring would fit around the circumference of a finger. Just as rings are manufactured in a wide range of sizes to fit various fingers, bands are manufactured in a wide range of sizes to fit various sized teeth. Once the proper band size is chosen for a particular tooth, it is then secured on the tooth by lining the inner surface of the band with a luting material, placing the band in the proper position around the circumference of the tooth, and allowing the luting agent to "dry" or harden. More succinctly, the band is simply glued, or cemented, to the tooth.

In order to fit and place a band on a particular tooth, it is first necessary to have access to the entire circumference of the tooth. Should a portion of the tooth remain obstructed or covered by the surrounding soft tissue, known as gingiva, it is first necessary to retract the obstructing tissue away from the tooth sufficiently to allow circumferential access. After the band is fitted and cemented, the tissue is allowed to relax to its original position, covering a portion of the band as well as the original portion of the tooth. Thus after cementation, some part of the band may remain in the narrow space (the "gingival sulcus") between the tooth and the gingiva.

Due to their anatomy, molars and premolars, collectively known as the posterior teeth, often pose a particularly difficult banding problem. The chewing surface (the "occlusal surface") of a posterior tooth contains a deep fissure or groove known as the "central groove" that traverses the length of this surface. When gingival tissue is found obstructing a portion of a posterior tooth near the central groove, a relatively wide segment of tissue may be found obstructing the tooth in the areas adjacent to the central groove, and an additional, much narrower segment of tissue often extends well into the central groove. Prior to fitting or cementing a band, this tissue must first be retracted to allow access to the full circumference of the tooth.

Currently existing dental tools and instruments, though not necessarily designed for tissue retraction, are often of appropriate shape and size to retract gingival tissues for the purposes of orthodontic banding. If tissue only needs to be retracted from the central groove, any instrument sufficiently narrow to fit into the groove could be used to retract this tissue. If there is no tissue in the central groove, there are several instruments adaptable to retracting wider segments of tissue away from a tooth surface. But when both the central groove and any other area are obstructed, a dilemma arises. Those instruments narrow enough to retract tissue from the central groove are insufficiently wide to adequately retract the remaining obstructing tissues. Those instruments wide enough to adequately retract larger segments of tissue cannot fit into the central groove to adequately retract this tissue. Such attempts, in fact, might actually crush or lacerate this thin piece of gingival tissue as the wider portions of tissue are retracted.

Several patents teach of instruments specifically designed for gingival tissue retraction for particular purposes. Each is designed of particular size, shape, and contour, as necessary to conform to the specific anatomy, both of the tooth and the tissue, involved, and to the particular procedure as required.

U.S. Pat. No. 4,004,345 teaches a rubber dam clamp with a separate arm designed for tissue retraction. While this arm may retract wider segments of tissue, there is no element for retracting the narrower portion of tissue lying in the central groove. In addition, even if tissue retraction were adequate, the clamp portion of this device would itself obstruct portions of the tooth that are required to be accessible for banding.

U.S. Pat. Nos. 5,358,403 and 5,899,694 teach gingival retraction by way of a loop of retraction cord that encircles the base of a tooth along the gumline or "gingival margin". These devices are designed to work by adapting snugly to the tooth. There is no feature in these designs for retracting tissue from the narrow central groove. If this type of retractor is employed to retract larger tissues near the occlusal surface of a tooth, portions of the tissue could simply lie over the retraction cord and continue to obstruct the tooth. Even if successful in pushing the tissue away from the tooth, the retraction cord itself would surround and obstruct the circumference of the tooth.

U.S. Pat. Nos. 5,022,859 and 5,718,583 teach instruments designed to retract gingival tissues in conjunction with the placement of retraction cord. While these instruments are narrow enough to potentially retract tissue in the central groove, they have no means of retracting wider segments of tissue.

U.S. Pat. No. 4,854,867 teaches a gingival retractor specifically shaped to conform to the contours of a tooth at the base of said tooth along the gingival margin. Tooth contours near the occlusal surface are significantly different, both in dimension and geometry, than those at the gingival margin. Though this device may be successful in retracting some wider tissues near the occlusal surface, its contour would prevent its universal application. Even if numerous instruments with varying contours were obtained, there is no means for retracting tissue from the central groove. Additionally, this device is designed to keep the tissue retracted by engaging the instrument edge firmly against the tooth. Once again, such application would itself obstruct access for banding.

Accordingly, each instrument currently available and used as a gingival retraction device has a number of deficiencies for the present application. There remains in the trade a need for a single properly sized and contoured instrument designed specifically for retracting gingival tissues away from the central groove and adjacent areas of a partially obstructed posterior tooth as necessary to allow complete circumferential access for the purpose of fitting and placing orthodontic bands.

SUMMARY OF THE INVENTION

It is therefore an object of the present invention to provide a novel dental tool for retracting gingival tissue that overcomes the problems experienced with prior devices.

Another object of the invention is to provide a gingival tissue retractor that is particularly suited to retracting tissue away from a posterior tooth for the fitting and placement of orthodontic bands.

Another object of the invention is to provide a gingival tissue retractor that is easy to use, is effective in operation, and is relatively inexpensive to manufacture.

These and other objects of the invention are achieved by providing a gingival tissue retractor having a working end that includes a first portion sufficiently narrow to retract tissue from the central groove of a posterior tooth, and an immediately adjacent and contiguous second portion sufficiently wide to retract tissue from the areas of the same tooth adjacent to the central groove. The device of the present invention is constructed of overall contour and dimensions sufficient to adapt closely and comfortably into the thin space, or sulcus, between the tissue and the adjacent tooth for the purposes of tissue retraction.

In the preferred embodiment of the invention, the tool is comprised of an elongated shaft or handle with the working end attached at one end thereof. The working end is generally curved, the second portion of the working end being formed at an apex of the curved working end, and the first portion being formed by a curved projection from the apex, the projection having a radius of curvature substantially smaller than the radius of curvature of the apex. The curved working end is preferably generally oval.

In an alternative embodiment of the invention, the working end can be formed generally in a diamond shape, with each operative side of the diamond-shaped working end formed of a triangle. The outwardly projecting apex of the triangle forms the first portion that is sufficiently narrow to retract tissue from a groove of a posterior tooth, and the immediately adjacent edges of the triangle widen quickly to form the second portion that is sufficiently wide to retract tissue from an adjacent area of the same tooth.

For versatility in use, both apices of the oval or diamond working end can be arranged with a first and second portion as described above. In addition, the oval or diamond working end is preferably concave to assist in conforming to the exterior surface of a tooth. If desired, the working end of the tool can be angled with respect to the axis of the shaft, and the shaft or handle can be formed with an angle to improve the comfort of a patient when the tool is used on posterior teeth and to permit the professional using the tool to position the tool in the proper location. With this arrangement, the tool of the present invention is suitable for either a right handed or left handed professional, or for use on either the right or left side of a patient's mouth, or on upper or lower teeth.

Although the tool of the present invention can be made of a metal material to be durable and easy to clean, in order to make the tool inexpensive and easy to manufacture, the tool is preferably molded as a single piece of a plastic material. The material can be either a high quality, heat resistant, sterilizable plastic so that the tool can be sterilized and reused, or it can be a less expensive non-sterilizable plastic so that it will be inexpensive enough to be discarded after a single use. In either case, the material is preferably pliable so that the tool will conform easily to a wide variety of shapes of teeth. If desired, the tool can be formed of a very inexpensive stiff plastic material in many shapes to provide versatility and still be economically viable because it is very inexpensive.

A method of retracting gingival tissue is also disclosed that involves placing a tool having a first narrow portion into a groove of a tooth, displacing tissue from the groove, moving a broader portion of the tool between the tissue and the tooth, and moving the tool away from the tooth to effect retraction of the tissue from the tooth. The method is preferably employed to retract gingival tissue from a groove and an adjacent surface of a posterior tooth without damaging either the tissue in the narrow groove or the broader layer of tissue covering the adjacent surface of the tooth.

Accordingly, when considering the advantages of the invention, the tissue retractor of the present invention far exceeds any existing product. It is a totally new retractor designed to solve the specific problems of retracting gingival tissues from both the central, or other, groove and adjacent areas of posterior teeth, simultaneously if needed, while minimizing the risk of harm to the associated tissue. No known product presently satisfies all these requirements.

These and other aspects of the invention will be more apparent from the following description of the preferred embodiments thereof when considered in connection with the accompanying drawings and appended claims.

BRIEF DESCRIPTION OF THE DRAWINGS

The present invention is illustrated by way of example and not limitation in the accompanying drawings in which like references indicate similar parts, and in which:

FIG. 3 is an enlarged, fragmentary, perspective view of the operating portion of the gingival tissue retractor of FIG. 1;

FIG. 4 is an enlarged, fragmentary, top view of the operating portion of an alternative embodiment of the gingival tissue retractor of the present invention;

FIG. 5 is an enlarged, fragmentary, top view of the operating portion of another alternative embodiment of the gingival tissue retractor of the present invention;

FIG. 6 is a front, elevational, fragmentary view of the gingival tissue retractor of FIG. 1; and FIG. 7 is a front, elevational, fragmentary view of an alternative embodiment of the gingival retractor of the present invention.

DETAILED DESCRIPTION OF THE PREFERRED EMBODIMENTS

Figure 1:
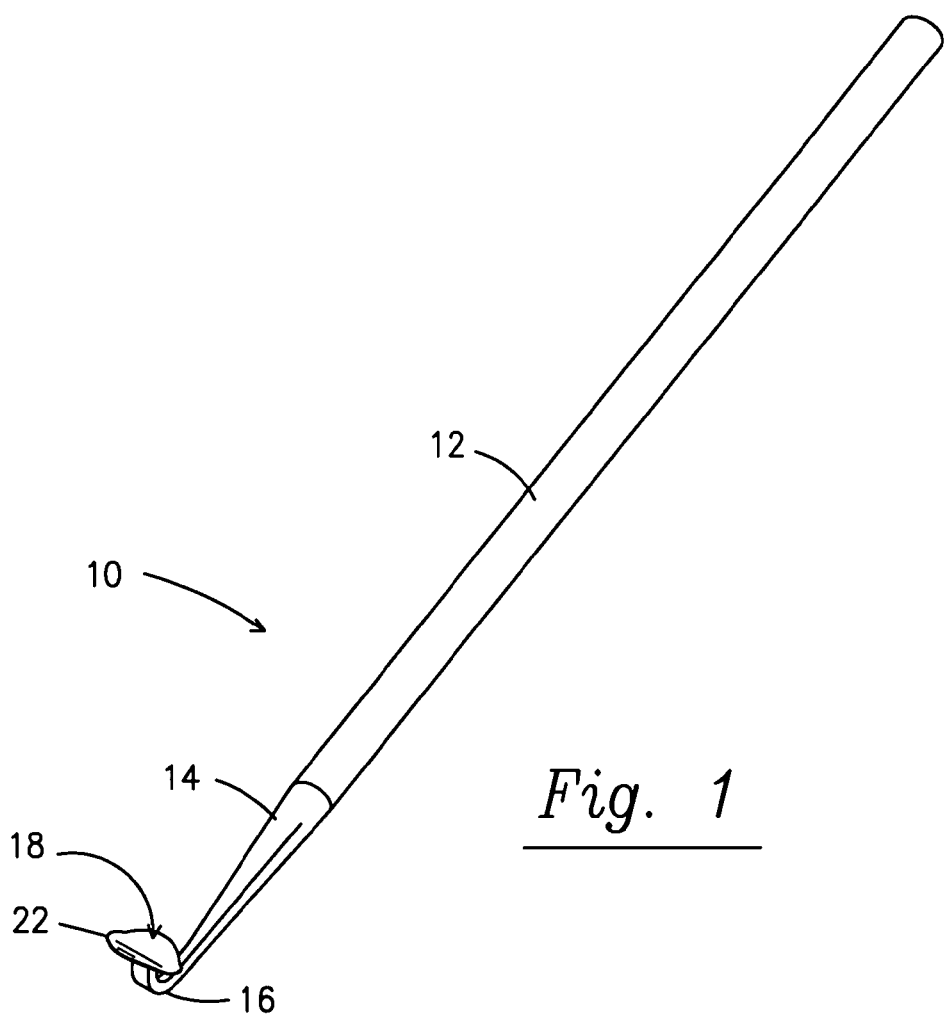
FIG. 1 is a perspective view of the gingival tissue retractor of the present invention.
Figure 2:
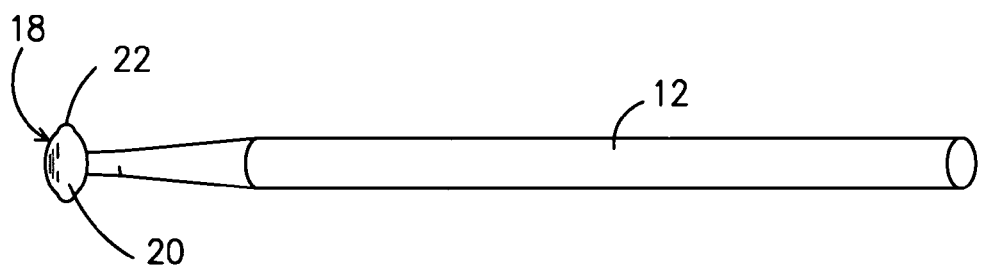
FIG. 2 is a top view of the gingival tissue retractor of FIG. 1.

A gingival tissue retraction tool is shown generally at 10 in FIG. 1 and is comprised of an elongated shaft 12 having a secondary end portion 14 terminating in a J-shaped curve 16 for supporting a working end 18. As can best be seen in FIG. 2, in the preferred embodiment of the invention, the working end 18 is generally curved, preferably oval in shape, with the long axis of the oval working end arranged generally perpendicular to the axis of the shaft 12. Additionally, if desired, the working end 18 of FIG. 1 can be angled with respect to the axis of the shaft. With this orientation, the apices 20 of the oval working end extend laterally from the shaft to provide working surfaces, as will be described later.

In the enlarged view of FIG. 3 it will be noted that each apex 20 of the oval working end 18 is provided with a small projection 22 that is convex and forms a leading edge working surface that is much narrower than the apex 20 of the working end 18. Thus, the apex 20 of the working end 18 has a relatively broad radius of curvature, and the small projection 22 has a substantially smaller radius of curvature which is convex in shape as depicted in FIGS. 1, 2, 3 and 4. More specifically, by way of example, if the radius of curvature of the apex 20 were on the order of 0.1 inches, the radius of the projection could be about half of that, or about 0.05 inches. Also it will be noted that the working end 18 is preferably concave in shape. This slight curvature in the face of the working end 18 helps the working end adapt to the shape of the gingival sulcus between the tooth and the gingiva.

The dental tool of the present invention is used to retract gingival tissue from a tooth. It is particularly useful in retracting gingival tissue from a groove in a tooth and then from an adjacent surface of that tooth. For example, the tool may be used to retract gingival tissue from the central groove on the occlusal surface of a posterior tooth and from an adjacent side surface of that tooth, such as the mesial or distal surface of the tooth. In addition, the tool may be used to retract gingival tissue from the facial or lingual groove of a posterior tooth, and from a side surface of the tooth adjacent the facial or lingual groove. Specifically, the wide portion of the working end 18 is placed sufficiently close to the narrow portion of the working end so that the wide portion of the working end 18 simultaneously engages the wider gingival tissue adjacent the posterior surface of the posterior tooth while still retracting the narrow tissue portion from the groove. This is necessary because during the fitting of oral appliances, once the gingival tissue is retracted from a groove in a tooth, the wide portion of gingival tissue may still obstruct the occlusal surface.

When in use, the narrow projection 22 is placed into the groove and the tissue is displaced away from the groove either by pushing the tissue away from the groove or by placing the narrow projection 22 between the gingival tissue and the tooth. Then the working end 18 is moved further between the tissue and the tooth so that the broader apex portion 20 engages gingival tissue covering a broader portion of the tooth adjacent the groove.

An alternative embodiment of the tissue retractor of the present invention is shown in FIG. 4. In this embodiment, the working end 18 is not oval. Rather, the major/long axis, which is generally perpendicular to the shaft 12, of the oval of the device shown in FIG. 1 has been angled forward by about 30 degrees with respect to the shaft to make the device more comfortable to use. For a similar purpose, as can best be seen in FIGS. 6 and 7, the secondary end portion 14 of the shaft 12 can be formed at an angle with respect to the shaft 12. It will be appreciated from the fragmentary view of FIG. 3 that the operative end of the retraction tool 10, including the secondary end portion 14 and the working end 18, could be formed at either end, or both ends, of the shaft 12. If these operative portions are formed at both ends of the shaft 12, the two working ends 18 could be of different sizes to make the tool useful for different sizes of teeth. In addition, if operative portions are formed at both ends of the shaft 12, the two working ends 18 could be oriented differently with respect to the shaft, for example, at different angles with respect to the shaft, to make the tool more versatile.

Lastly, although the preferred embodiment of the present invention has been illustrated and described, it is also possible to practice the present invention with a working end of the tool that has a simpler shape. More specifically, as can be seen in FIG. 5, the working end 24 can be formed generally in a diamond shape providing two oppositely facing, generally triangular operative portions 26. The apex 26 are functional equivalents of the small projections 22 of FIGS. 1–4 and are convex in form. Further, the apex of each triangular portion provides the narrow first portion of the tool discussed above, and as the triangular portion of the tool broadens, the broader portion 28 provides the second portion of the tool capable of retracting gingival tissue covering a broader, lateral surface of the tooth.

Although the gingival retraction tool 10 can be made of a metal material to be durable and easy to sterilize for re-use, in order to make the tool inexpensive and easy to manufacture, the tool is preferably molded as a single piece of a plastic material. The material can be either a high quality, heat resistant, sterilizable plastic so that the tool can be sterilized and reused, or it can be a less expensive non-sterilizable plastic so that it will be inexpensive enough to be discarded after a single use. In either case, the material is preferably pliable so that the tool will conform easily to a wide variety of shapes of teeth. If desired, the tool can be formed of a very inexpensive stiff plastic material in many shapes to provide versatility and still be economically viable because it is very inexpensive.

The method of the present invention for retracting gingival tissue involves placing a tool having a first narrow portion into a groove of a tooth, displacing tissue from the groove, moving a broader portion of the tool between the tissue and the tooth, and moving the tool away from the tooth to effect retraction of the tissue from the tooth. The method is preferably employed to retract gingival tissue from a groove and then from an adjacent surface of a posterior tooth without damaging either the tissue in the narrow groove or the broader layer of tissue covering the adjacent surface of the tooth.

Although the gingival tissue retractor of the present invention is described for use in connection with orthodontics, and is particularly suited for use in orthodontics, the special properties and design of the retractor may render it suitable for use in a number of other medical, dental, and scientific applications.

Various modifications and changes may be made by those having ordinary skill in the art without departing from the spirit and scope of this invention. Therefore, it must be understood that the illustrated embodiments of the present invention have been set forth only for the purpose of example, and that they should not be taken as limiting the invention as defined in the following claims.

The words used in this specification to describe the present invention are to be understood not only in the sense of their commonly defined meanings, but to include by special definition, structure, material, or acts beyond the scope of the commonly defined meanings. The definitions of the words or elements of the following claims are, therefore, defined in this specification to include not only the combination of elements which are literally set forth, but all equivalent structure, material, or acts for performing substantially the same function in substantially the same way to obtain substantially the same result.

In addition to the equivalents of the claimed elements, obvious substitutions, now or later known to one of ordinary skill in the art, are defined to be within the scope of the defined elements.

The claims are thus to be understood to include what is specifically illustrated and described above, what is conceptually equivalent, what can be obviously substituted, and also what incorporates the essential idea of the invention.

Now that the invention has been described,

I claim:

1. A dental tool for facilitating tissue retraction comprising:
    a shaft terminating in a working end member, said working end member having an operative end including a first portion sufficiently narrow to retract tissue from a groove of a tooth, and said operative end including a second portion adjacent said first portion, said second portion being sufficiently wide to retract tissue from an area of said tooth adjacent said groove; and
    wherein said operative end is generally curved, said second portion being formed by an apex of the generally curved operative end, said apex having a radius of curvature, and said first portion being formed by a curved projection from said apex, said curved projection having a radius of curvature substantially smaller than the radius of curvature of said apex.

2. The dental tool of claim 1 wherein said groove is a central groove of a posterior tooth.

3. The dental tool of claim 1 wherein said groove is a facial or lingual groove of a posterior tooth.

4. The dental tool of claim 1 wherein said operative end is generally triangular.

5. The dental tool of claim 1 wherein said working end is generally diamond shaped.

6. The dental tool of claim 1 wherein said shaft has a secondary end portion that is angled with respect to said shaft.

7. The dental tool of claim 1 wherein a working end is formed at both ends of said shaft.

8. The dental tool of claim 7 wherein said working ends at both ends of said shaft are of different sizes.

9. The dental tool of claim 7 wherein said working ends at both ends of said shaft are of different orientation with respect to the shaft.

10. The dental tool of claim 1 wherein said tool is comprised of a metal material.

11. The dental tool of claim 1 wherein said tool is comprised of a plastic material.

12. The dental tool of claim 11 wherein said tool is comprised of a heat resistant plastic material.

13. A dental tool for facilitating tissue retraction comprising:
    a shaft terminating in a working end member, said working end member having an operative end including a first portion sufficiently narrow and convex to retract tissue from a groove of a tooth, and said operative end including a second portion adjacent said first portion, said second portion being sufficiently wide to retract tissue from an area of said tooth adjacent said groove; and
    wherein said working end member is generally oval, said second portion being formed by an apex of said oval, said apex having a radius of curvature, and said first portion being formed by a curved projection from said apex, said curved projection having a radius of curvature substantially smaller than the radius of curvature of said apex.

14. The dental tool of claim 13 wherein said generally oval working end member is attached to the shaft near the center of said oval and is arranged generally perpendicular to said shaft, and both apices of the oval include curved projections therefrom, each of said curved projections having a radius of curvature smaller than the radius of curvature of the apex from which they project.

15. The dental tool of claim 14 wherein said generally oval working end member is concave.

16. The dental tool of claim 14 wherein said apices form an angle with the perpendicular to the shaft.

17. A dental tool for facilitating tissue retraction comprising:
    a shaft terminating in a working end member, said working end member having an operative end including a first portion sufficiently narrow to retract tissue from a groove of a tooth, and said operative end including a second portion adjacent said first portion, said second portion being sufficiently wide to simultaneously retract tissue from an area of said tooth adjacent said groove; and
    said working end member is generally oval, said second portion being formed by an apex of said oval, said apex having a radius of curvature, and said first portion being formed by a curved projection from said apex, said curved projection having a radius of curvature substantially smaller than the radius of curvature of said apex.

18. The dental tool of claim 17 wherein said generally oval working end member is attached to the shaft near the center of said oval and is arranged generally perpendicular to said shaft, and both apices of the oval include curved projections therefrom, each of said curved projections having a radius of curvature smaller than the radius of curvature of the apex from which they project.

19. The dental tool of claim 18 wherein said generally oval working end member is concave.

20. The dental tool of claim 18 wherein said apices form an angle with the perpendicular to the shaft.

* * * * *